United States Patent [19]

Kress et al.

[11] Patent Number: 5,783,709
[45] Date of Patent: Jul. 21, 1998

[54] STEREOSELECTIVE PROCESS FOR MAKING SUBSTITUTED AMINO ACID DERIVATIVES

[75] Inventors: Michael Kress, Somerset; Chunhua Yang, Edison; Nobuyoshi Yasuda, Mountainside, all of N.J.

[73] Assignee: Merck & Co., Inc., Rahway, N.J.

[21] Appl. No.: 918,294

[22] Filed: Aug. 25, 1997

Related U.S. Application Data

[60] Provisional application No. 60/029,436 Oct. 31, 1996.
[51] Int. Cl.$^6$ ................................................ C07D 207/16
[52] U.S. Cl. ............................................ 548/535; 548/532
[58] Field of Search ................................. 548/532, 535

[56] References Cited

U.S. PATENT DOCUMENTS 5,413,999  5/1995  Vacca et al. ................... 514/231.5
5,627,202  5/1997  DeSolms ........................ 514/397

OTHER PUBLICATIONS

J. Y. L. Chung et al., *J. Org. Chem.* 55, pp. 270–277 (1990).

D. A. Evans et al., *J. Am. Chem. Soc.*, 109, pp. 1751–7158 (1987).

ABE et al., S. *J. High Res. Chromo. Comm.*, pp. 549, (1981).

*Primary Examiner*—Robert W. Ramsuer
*Assistant Examiner*—Dominic Keating
*Attorney, Agent, or Firm*—Sylvia A. Ayler; Mark R. Daniel

[57] ABSTRACT

The invention encompasses a method for the stereoselective synthesis of alkyl proline and other amino acid derivatives which are intermediates of the farnesyl-protein transferase inhibiting $CA^1A^2X$ motif of the protein Ras. The instant process employs an efficient diastereoselective [2,3]-Wittig rearrangement of α-allyloxy amide enolates mediated by a chiral auxiliary to provide acyclic and cyclic precursors.

4 Claims, No Drawings

STEREOSELECTIVE PROCESS FOR MAKING SUBSTITUTED AMINO ACID DERIVATIVES

This application claims the priority benefit of provisional application Ser. No. 60/029,346 filed Oct. 31, 1996.

BACKGROUND OF THE INVENTION

During the development of a commercially viable asymmetric synthesis of potent $CA^1A^2X$ analogs which inhibit farnesyl-protein transferase and are useful in the treatment of cancer, a highly stereoselective synthesis of a key intermediate, a substituted proline derivative, needed to be developed. A variety of methods of general applicability have been worked out by Chung, J. Y. L., et al. *J. Org. Chem* 1990, 55, 270–27. We have found that the previously disclosed process requires resolution of enantiomers, costly starting materials and does not provide adequate control over the pyrrolidine ring relative stereochemistry. Accordingly, an alternative processes to obviate the difficulties is desired.

SUMMARY OF THE INVENTION

This invention encompasses a method for the stereoselective synthesis of alkyl prolines of the general Formula I, intermediates of the farnesyl-protein transferase inhibiting CA1A2X motif of the protein Ras, via the intermediacy of novel hydroxy-amides of the general Formula Ia.

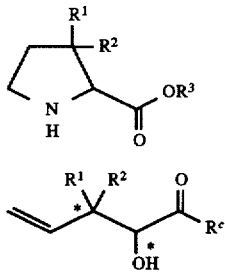

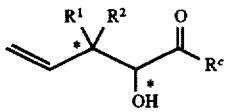

The instant process employs an efficient diastereoselective [2,3]-Wittig rearrangement of enolates derived from α-allyloxy amides of the general formula 1, wherein $R^c$ denotes a nitrogen containing chiral auxiliary and $R^1$ and $R^2$ are independently selected from the group consisting of H, $C_{1-6}$ alkyl and aryl. The products of the rearrangement (i.e., compounds of Ia) are then subjected to an intramolecular hydroboration/cycloalkylation reaction as disclosed by Evans, D. A. et al. *J. Am. Chem. Soc.* 1987, 109, 7151–7158 which allows for retention of the pre-existing acyclic stereochemistry of the alkyl proline products. The instant process eliminates the need to resolve enantiomers, provides more precise control over the pyrrolidine ring relative stereochemistry and more cost-effectively utilizes starting materials. This invention also relates to the novel compounds of formula Ia

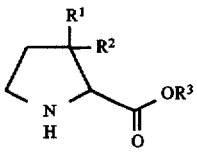

which are products of the [2,3]-Wittig rearrangement.

DETAILED DESCRIPTION OF THE INVENTION

The instant process is generally depicted in Scheme 1 below.

Scheme 1

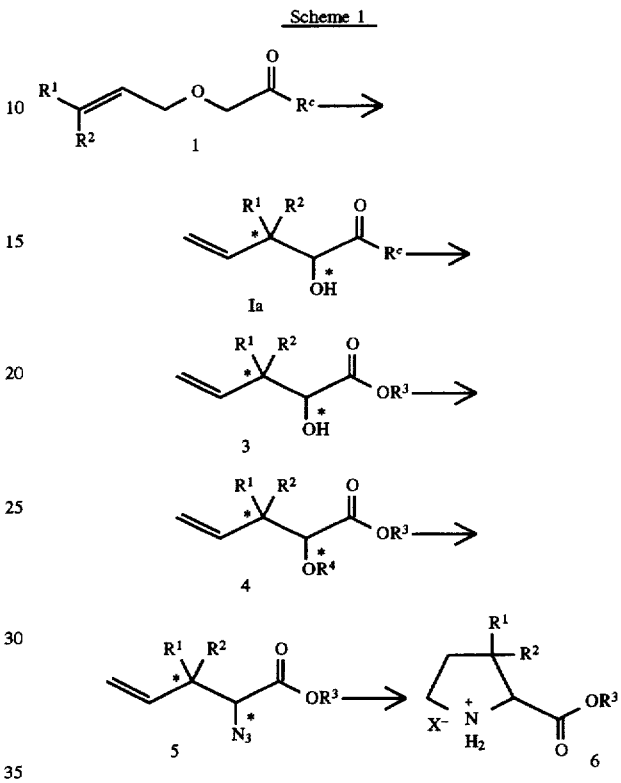

wherein X is a salt.

One aspect of the instant invention relates to a method of preparing a compound of formula I

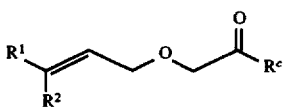

or its pharmaceutically acceptable salt, wherein:

$R^1$ and $R^2$ are independently selected from the group consisting of H, $C_{1-6}$ alkyl, and aryl, and $R^3$ is selected from the group consisting of H, $C_{1-6}$ alkyl, aryl and allyl, which comprises:

rearranging a compound of formula 1:

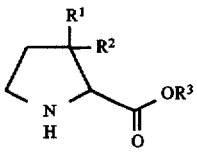

through reaction with a strong base at an initial temperature of about –100° C. to about –50° C., preferably about –85° C. to about –70° C., followed by aging at this temperature for about 30 minutes to about 6 hours; after this initial period, the mixture is heated to a secondary temperature of about –50° C. to about 0° C., preferably about –45° C. to about –20° C. and aged for a at least thirty minutes to provide a compound of formula Ia,

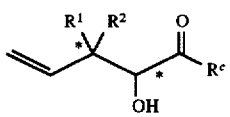

wherein:

$R^2$ and $R^3$ are described above. $R^c$ is a chiral auxiliary and* designates a stereogenic center;

esterifcation of Ia with an acidic alcohol for about 30 minutes to about 3 hours to give a compound of formula 3;

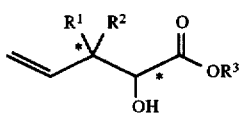

functionalization of the hydroxy group of 3 using a tertiary amine to provide a compound of formula 4,

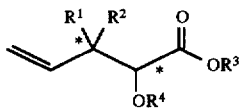

wherein $OR^4$ is a leaving group such as Omesylate, Otosylate, Otriflate and the like;

displacing the $OR^4$ group of formula 4 with sodium azide in the presence of a polar aprotic solvent at a temperature of about 40° C. to about 140° C., preferably, 50° C. to 80° C. to produce a compound of formula 5;

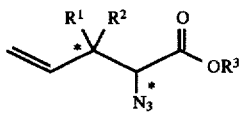

and, hydroboration and cycloalkylation of formula 5 with a dialkylborane reagent followed by treatment with an acid to give a compound of formula I or its pharmaceutically acceptable salt

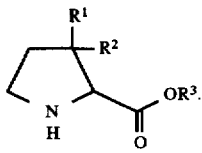

Another aspect of the invention is a method of making a compound of formula II

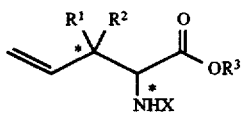

wherein:

$R^1$ and $R^2$ are independently selected from the group consisting of H, $C_{1-6}$ alkyl, and aryl, $R^3$ is selected from the group consisting of H, $C_{1-6}$ alkyl, aryl and allyl, and X is a nitrogen protecting group.

which comprises rearranging a compound of formula 1:
rearranging a compound of formula 1:

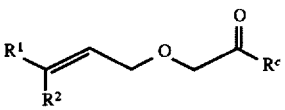

through reaction with a strong base at an initial temperature of about −100° C. to about −50° C., preferably about −85° C. to about −70° C., followed by aging at this temperature for about 30 minutes to about 6 hours; after this initial period, the mixture is heated to a secondary temperature of about −50° C. to about 0° C., preferably about −45° C. to about −20° C. and aged for a at least thirty minutes to provide a compound of formula Ia,

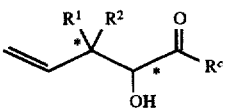

wherein:

$R^2$ and $R^3$ are described above. $R^c$ is a chiral auxiliary and* designates a stereogenic center;

esterifcation of Ia with an acidic alcohol for about 30 minutes to about 3 hours to give a compound of formula 3;

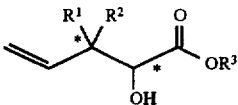

functionalization of the hydroxy group of 3 using a tertiary amine to provide a compound of formula 4,

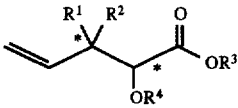

wherein $OR^4$ is a leaving group such as Omesylate, Otosylate, Otriflate and the like;

displacing formula 4 with sodium azide in the presence of a polar aprotic solvent at a temperature of about 40° C. to about 140° C., preferably, 50° C. to 80° C. to produce a compound of formula 5;

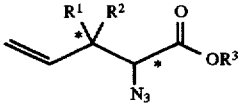

reducing compound 5 with a reducing agent in the presence of an aqueous acid, followed by treatment with a nitrogen protecting group belonging to the group consisting of Boc, Bn, Alloc, FMOC, acetate, and BOM to give a compound of formula II

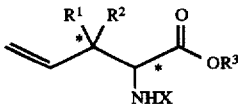

Yet another aspect of this invention is a compound of formula Ia

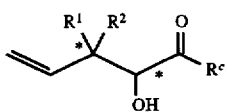

wherein:

wherein R¹ and R² are independently selected from the group consisting of H, $C_{1-6}$ alkyl and aryl and $R^c$ selected from the group consisting of

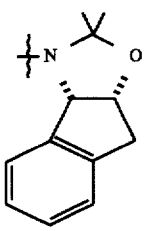

,

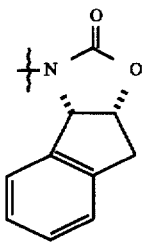

,

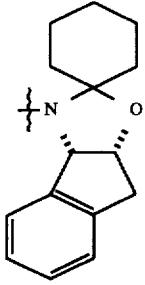

,

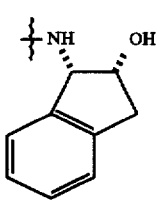

and

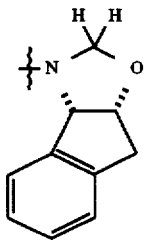

The rearrangement step can be carried out in organic solvents such tetrahydrofuran (THF), toluene, xylenes, dimethylforamide, Et₂O, DME and the like, preferably THF and Et₂O and requires the use of about 0.5 to about 3.0 equivalents, preferably about 1.0 to about 2.5 equivalents of a strong base such as LDA, NaH, KH, LHMDS, n-BuLi, NaHMDS, KHMDS and the like, preferably LHMDS or LDA. Additives (about 0.5 equivalents to about 30 equivalents, preferably about 1.0 to about 18 equivalents, more preferably about 1.0 to about 7 equivalents) such as $CP_2ZrCl_2$, HMPA, TMEDA, DMPU and the like, preferably HMPA are useful in this rearrangement step and therefore may optionally be added. The concentration of formula 1 can range from about 0.05 to about 0.3M. The preferred initial temperature range for the rearrangement step is –85° C. to about –70° C. which is maintained for about 30 minutes to about 6 hours, at which point the mixture is heated to a preferably temperature of about –15° C. to about –5° C.

The esterification step can be carried out using refluxing acidic aqueous alcohol, wherein the acidic alcohol is about a 3 to 1 ratio of alcohol to acid, wherein the alcohol is selected from a group consisting of methanol, ethanol, propanol, butanol, benzyl and isopropanol and the acid can be selected from a group consisting of anhydrous HCl, HCl, TsOH, MsOH, sulfuric acid and the like. The esterification step can optionally be accomplished in two steps via known acid alkylation with an alkylating agent such as diazomethane and the like.

The functionalization step can be carried out by functionalizing the hydroxy group of formula 3 as its mesylate or tosylate using for example a tertiary amine base such as triethylamine, diisopropylethylamine, dimethylethylamine, and dimethylpentylamine and the like followed by displacement with sodium azide in the presence of a polar aprotic solvent such as DMSO, DMF and the like at a temperature of about 40° C. to about 140° C., preferably, about 50° C. to about 80° C. to produce a compound of formula 5.

The hydroboration/cycloalkylation steps are known and can be carried out, for example, by using a dialkylborane reagent such as dicyclohexylborane, 9-BBN and the like, preferably dicyclohexylborane in the presence of an organic solvent such as THF, toluene, xylenes, dimethylforamide, Et₂O, DME and the like, preferably THF, followed by treatment with an aqueous acid such as 1N to 12N HCl or 1N to 18N $H_2SO_4$.

The reduction and protection steps are also known and can be carried out, for example, using a reducing agent such as triphenylphosphine (PPh3) and an aqueous acid such as 1N to 12N HCl or 1N to 18N $H_2SO_4$ in the presence of an organic solvent such as THF, or alternatively by known catalytic hydrogenation methods, followed by treatment with a nitrogen protecting reagent to incorporate a nitrogen protecting group.

The sequence and conditions of the reaction steps is dependant on the structure and functional groups present. The protecting groups that are necessary and may be chosen with reference to "Protecting Groups in Organic Synthesis, Greene T. W., Wiley-Inerscience, New York, 1981". The blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable nitrogen protecting groups are: carbobenzyloxy, t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl and the like.

A chiral auxilary is defined as an easily removable chiral group of known absolute stereochemistry which is attached at a position near the site of reation and is capable of influencing the stereochemical outcome of the reaction of interest. Some of the chiral auxiliaries useful in this method are:

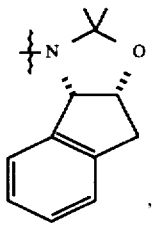

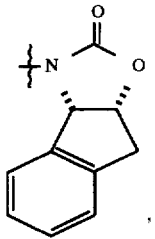

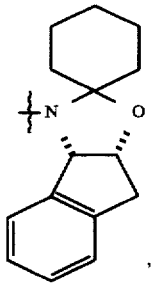

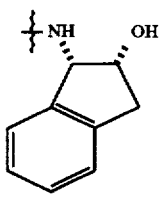

and

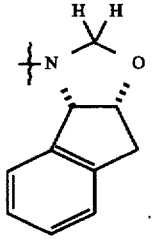

A preferred chiral auxiliary useful in this invention is wherein $R^c$ is (1S,2R)-1-amino-indan-2-ol:

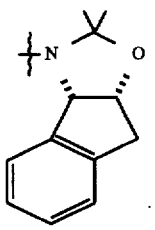

As used herein, "alkyl" is intended to include branched, cyclic and straight-chain saturated aliphatic hydrocarbon groups having the specified number of carbon atoms. Examples of cycloalkyl groups include cyclopropyl, cyclobutyl, cyclopentyl, cyclohexyl and the like.

As used herein, "aryl" is intended to include aryls and heteroaryls, both substituted and unsubstituted, which are defined as carbazolyl, furyl, thienyl, pyrrolyl, isothiazolyl, imidazolyl, isoxazolyl, thiazolyl, oxazolyl, pyrazolyl, pyrazinyl, pyridyl, pyrimidyl, purinyl or quinolinyl as well as aromatic rings e.g., phenyl, substituted phenyl and like groups as well as rings which are fused, e.g., naphthyl and the like. Substitution can be 1 to 3 groups of $C_{1-6}$ alkyl, hydroxy, halogen, carbonyl, $CO_2$, $NO_2$, $OC_{1-6}$ alkyl; $SC_{1-6}$ alkyl, $N(C_{1-6}$ alkyl$)_2$ and the like.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isothionic, trifluoroacetic and the like.

It is understood that substituents and substitution patterns on the compounds of the instant invention can be selected by one of ordinary skill in the art to provide compounds that are chemically stable and that can be readily synthesized by techniques known in the art as well as those methods set forth below.

Abbreviations used in the description of the chemistry and in the Examples that follow are:

Ac$_2$O Acetic anhydride;
Boc t-Butoxycarbonyl;
n-BuLi n-butyl lithium;
Cp cyclopropyl;
DBU 1,8-diazabicyclo[5.4.0]undec-7-ene;
DMAP 4-Dimethylaminopyridine;
DME 1,2-Dimethoxyethane;
DMF Dimethylformamide;
DMPU 1,3-dimethyl-3,4,5,6-tetrahydro-2(1H)-pyrimidinone
EDC 1-(3-dimethylaminopropyl)-3-ethyl-carbodiimide-hydrochloride;
HMPA Hexamethylphosphoramide
HOBT 1-Hydroxybenzotriazole hydrate;
Et$_3$N Triethylamine;
EtOAc Ethyl acetate;
FAB Fast atom bombardment;
HOOBT 3-Hydroxy-1,2,2-benzotriazin-4(3H)-one;
HPLC High-performance liquid chromatography;
KHMDS Potassium bis(trimethylsilyl)amide;
LHMDS Lithium bis(trimethylsilyl)amide;
MCPBA m-Chloroperoxybenzoic acid;
MsCl Methanesulfonyl chloride;
NaHMDS Sodium bis(trimethylsilyl)amide;
Py Pyridine;
TFA Trifluoroacetic acid;
THF Tetrahydrofuran;

TMEDA Tetramethylethylene diamine
TMS Trimethylsilane.

EXAMPLES

Examples provided are intended to assist in a further understanding of the invention. Particular materials employed, species and conditions are intended to be further illustrative of the invention and not limitative of the reasonable scope thereof.

Example 1

The amide-acetonide 3 chiral auxiliary wherein $R^c$ is (1S, 2R)-1-amino-indan-2-ol can be made on 0.5 mole scale as described in scheme 2

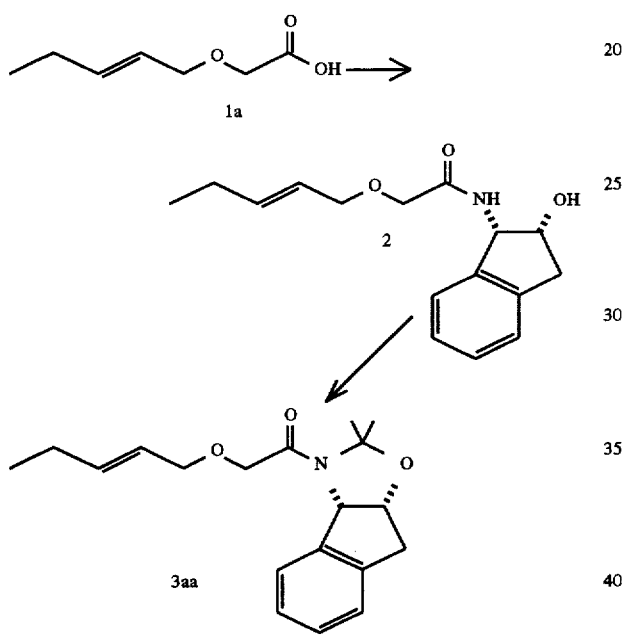

A THF suspension of NaH (60% in mineral oil) at 0° C., was sequentially treated with THF solutions of trans-2-penten-1-ol and bromoacetic acid over a 1 hour period. Upon completion of the additions the resultant thick reaction mixture was heated to reflux for 8 hours. After aqueous quench, acid/base extration and distillation, an 80% yield of 1a was obtained. Activation of 1a was achieved in iPAc using Vilsmeier conditions (POCl₃, DMF). The resultant iPAc solution was used directly under Schotten Baumann conditions (2.5 NaOH) to acylate (1S,2R)-1-amino-indan-2-ol. Hydoxy-amide 2 was isolated after concentration of the iPAc layer and trituration of the crude solids with cold pentane (73% yield from 1a). Treatment of 2 with methoxypropene and catalytic MeSO₃H, in iPAc, gave a 94% yield of amide 3aa [b.p.=223°–230° C., 9 torr; $[\alpha]^{23}D=+144°$ (c2.0, CHCl₃)]. (1S,2R)-1-amino-indan-2-ol and the process thereof are known and can be found in U.S. Pat. No. 5,413,999 granted to Vacca et al.

Example 2

The generality of the reaction was assessed by the use of a variety of enolate counter ions, reaction solvents and additives for the rearrangement of 3aa below. (Table 1).

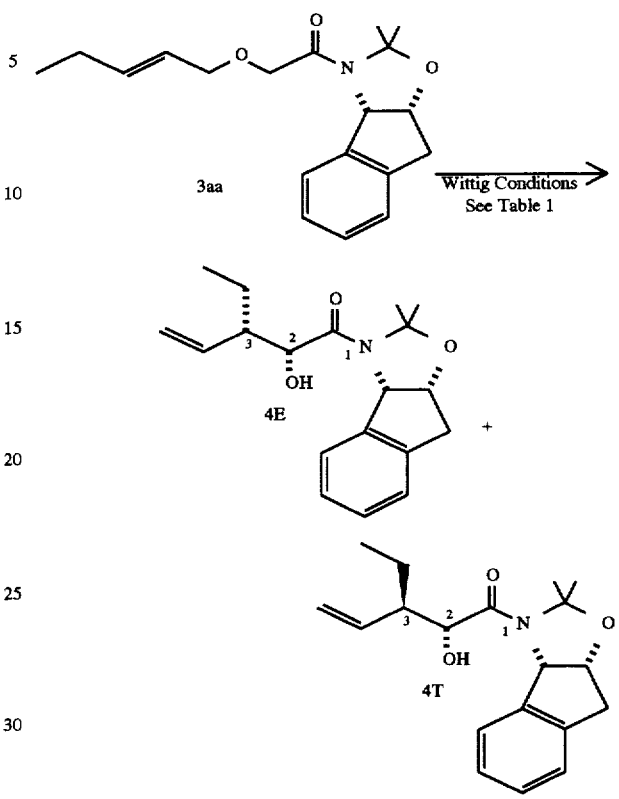

TABLE 1

| Entry[a] | Base | Solvent | Additive (equiv.) | %4E (2R,3S) | %4T (2R,3R) | Assay Yield of 4E + 4T |
|---|---|---|---|---|---|---|
| 1 | LHMDS | THF | none | 79 | 21 | 95%[c] |
| 2 | LHMDS | Et₂O | none | 78 | 22 | 93%[c] |
| 3 | KHMDS | THF | none | 66 | 34 | 91%[c] |
| 4 | NaHMDS | THF | none | 73 | 27 | 80% |
| 5 | n-BuLi | THF | none | 76 | 24 | 94%[c] |
| 6[b] | n-BuLi | THF | Cp₂ZrCl₂(1.2) | 94 | 7 | 73% |
| 7 | LHMDS | THF | HMPA(3.0) | 86 | 14 | 95%[c] |
| 8 | LHMDS | THF | HMPA(5.0) | 87 | 13 | 96%[c] |
| 9 | LHMDS | THF | HMPA(10.0) | 88 | 12 | 95%[c] |
| 10 | LHMDS | THF | HMPA(15.0) | 89 | 11 | 97%[c] |
| 11 | LHMDS | THF | TMEDA(10.0) | 80 | 20 | 90%[c] |
| 12 | LHMDS | THF | DMPU(16.0) | 85 | 15 | 92%[c] |

[a]Except when noted, all reactions were run at a concentration of 0.1M, with 1.5 equivalents of base, at an initial reaction temperature of −78° C. The reaction mixture was subsequently aged for 2 hours at this temperature, warmed to −10° C. over the course of approximately 2 hours and assayed by GC.
[b]1.2 equivalents of base were used.
[c]For entries 1–3, 5 and 7–12 the remaining materials consisted of one diasteromer of [2,3] rearrangement as determined by ¹H and ¹³C NMR. On a preparative scale this minor product was cleanly separated by silica gel chromatography.

[2,3] rearrangement of the lithium enolate of amide-acetonide 3aa provided a greater than 98% assay yield of products resulting from [2,3] sigmatropic rearrangement (Table 1, entry 1). See Nakai et al., *Organic Reactions*, vol. 46, John Wiley & Sons, Inc.; New York, N.Y.; 1994; pp 105–210 for a review of the [2,3]-Wittig rearrangement. The diastereoselectivity for the rearrangement of the enolate of 3aa was observed to be a function of enolate counter ion, with erythro selectivity increasing from K<Na<Li<Zr (Table 1). Although selectivity favoring 4E was highest using Katsuki's zirconium enolate protocol, there was a reduction in the conversion of 3aa. Modification of this protocol (increasing n-BuLi to 2.0 equivalent) lead to consumption of 3aa, however a low assay yield of 4E, and 4T was still observed.

Using LHMDS as a base and employing HMPA as an additive, resulted in higher levels of erythro selectivity than in the absence of HMPA (Table 1, entry 1 vs. entries 7 through 10). Unlike the zirconium enolate case, the enhanced levels of diastereoselectivity observed in the presence of HMPA did not come at the expense of assay yield. Optimal selectivity on a 1 mmol scale was obtained using 15 equivalents of HMPA (Table 1, entry 10), a level of HMPA deemed unacceptable on large scale.

Reducing the HMPA charge to 5 equivalents on a 0.2 mol scale resulted in an acceptable compromise between diastereoselectivity and level of HMPA (91% assay yield of [2,3] products containing the 2R configuration: 86% 4E: 14% 4T). The reaction was quenched with 0.1N sodium phosphate buffer (pH=6.8) and the aqueous layer extracted with iPAc. The organic layer was washed three times with $H_2O$ to remove the residual HMPA and concentrated to give a yellow-orange oil. Filtration through a short deactivated silica gel column (8 X weight of crude oil, 1% $Et_3N$ in 10% EtOAc in hexane) gave 80% yield of a 85:15 4E:4T mixture as an oily solid. Further enrichment in 4E was achieved by trituration with pentane (4° C.) to give an overall 67% yield (94:6 4E:4T) from 3aa as a white powder. Both amide 3aa and hydroxy-amide 4E exist at room temperature, in $CDCl_3$, as a 97:3 mixture of rotomers as determined by magnetization transfer upon irridation of the H1' proton of the aminoindanol auxiliary.

The stereochemistry of 4E was determined by a X-ray diffraction study as (2R,3S). An analytically pure sample of 4E [white crystalline, m.p.=97.5°–98° C., [α]23D=+133° (c1.0, $CHCL_3$)] was available by normal phase, preparative HPLC on a YMC-pak CN column. The (2R,3R) stereochemistry of 4T was deduced by removing the C.3 stereocenter via olefin hydrogenation of a 9:1 4E:4T mixture (10% Pd/C, EtOH). The resultant product was determined to be diastereomerically pure by $^1H$, and $^{13}C$ NMR.

The diastereomeric ratios of 4E:4T were routinely assayed on a HP 6890 GC with FID, using a splitless injection of a heptane solution onto a 5m HP-1/30 DB-23 joined column.

Example 3

The following amide-acetonides 13–17 were also made available following the previously described method, and their respective [2,3]-Wittig rearrangements carried out under identical conditions (Table 2).

Scheme 4

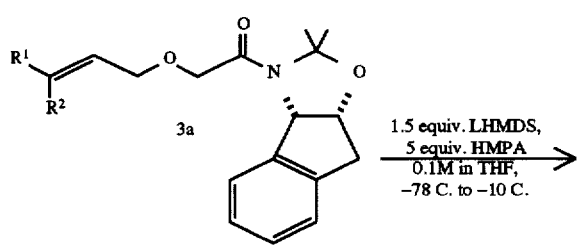

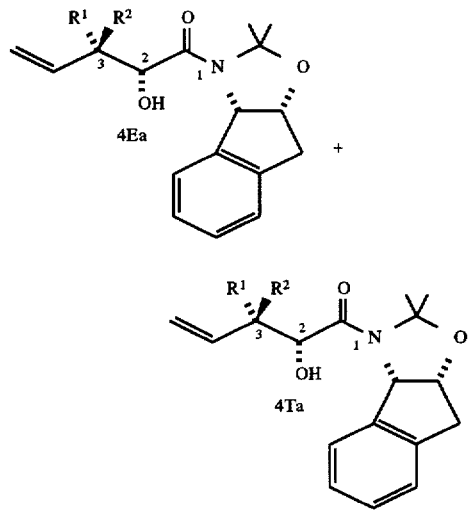

TABLE 2

| Entry | R³ | R² | Crude Assay Yield | Major (Config.) | Minor (Config.) | Isolated Yield (4Ea:4Ta) |
|---|---|---|---|---|---|---|
| 13 | H | Me | 97% | 90% (2R,3S) | 10% (2R,3R) | 67% (94:6) |
| 14 | H | Et | 96% | 87% (2R,3S) | 13% (2R,3R) | 67% (94:6) |
| 15 | Et | H | 93% | 32% (2R,3S) | 68% (2R,3R) | not attemped |
| 16 | H | H | 95% | >98% (2R) | NA | 88% (NA) |
| 17 | H | Ph | 87% | 91% (2R,3R) | 9% (2R,3S) | 68% (93:7) |

Generally, the entries possessing the trans-disubstituted geometry (entries 13, 14 and 17) afforded excellent selectivity for 2R,3S configuration (erythro). The rearrangement of the lithium enolate of amide 15, containing a cis-disubstituted olefin geometry, ed in lower 2R,3R selectivity (ca. 2:1 threo:erythro). Amide 16, possessing a terminal olefin, afforded greater than 98% 2R selectivity. The absolute stereochemistry of the [2,3]-Wittig rearranged products of amides 13 and 16 were determined after conversion to L-isoleucine and L-norvaline, respectively, followed by GC comparison of their trifluoracetamide methyl esters to authentic samples on a Alltech Chirasil-Val column (25m) as per: Abe et al., *S. J. High Res. Chromo. Comm.* 1981, 549.

Example 4

The utility of the [2,3]-Wittig products can be demonstrated, for example, by converting 4E to functionalized amino acids 11 and 12 as depicted in Scheme 5.

Scheme 5

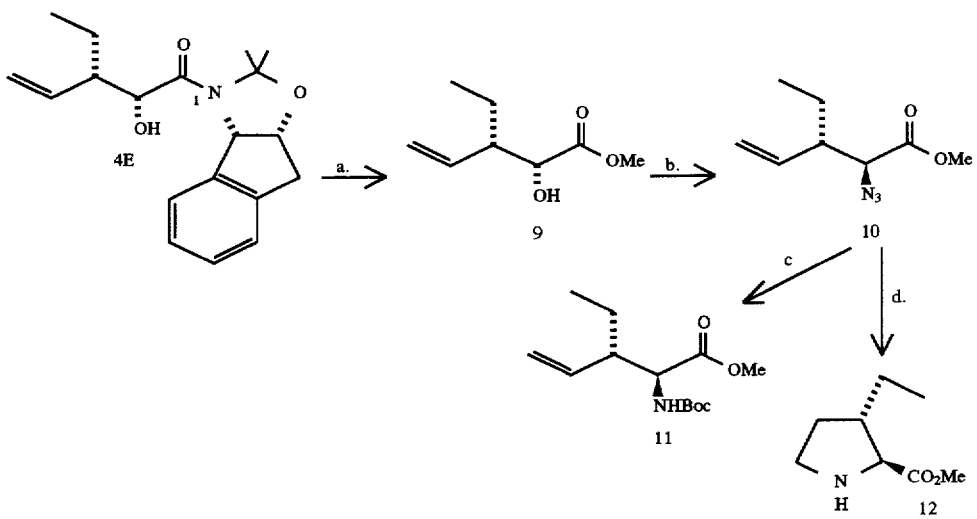

Reagents and conditions: a. MeOH: 12N HCl (3:1), 1 hour (74%); b. i) MsCl, Et$_3$N, CH$_2$Cl$_2$ (92%), ii) NaN$_3$, DMSO (76%); c. i) PPh$_3$, 1N HCl, THF, ii) Boc$_2$O, 5N NaOH, THF (80%); d. Cx$_2$BH, THF, then 1N HCl, (78%).

Auxiliary solvolysis was routinely carried out on a 94:6 ratio of 4E:4T or better, and was achieved in refluxing aqueous methanol (3:1 v/v MeOH: 12N HCL) to afford a 74% distilled yield of hydroxy-methyl ester 9 with a 90% HPLC assay recovery of amino-indanol. Conversion of 9 to azide 10 occurred in two steps under standard conditions (overall 70% yield). Reduction of 10 under Staudinger conditions and Boc protection of the crude amine gave 11 in 80% yield after purification. Alternatively, treatment of 10 with dicyclohexylborane afforded (2S,3S)-3-ethyl proline HCL 12 in 78% yield after acidic hydrolysis of the intermediate aminoborane with aqueous HCL (Azide 10 (92% de) underwent hydroboration-cycloalkylation to afford 12 as a 88:12 (76% de) mixture of trans:cis proline ring isomers, as determined by $^1$H NMR).

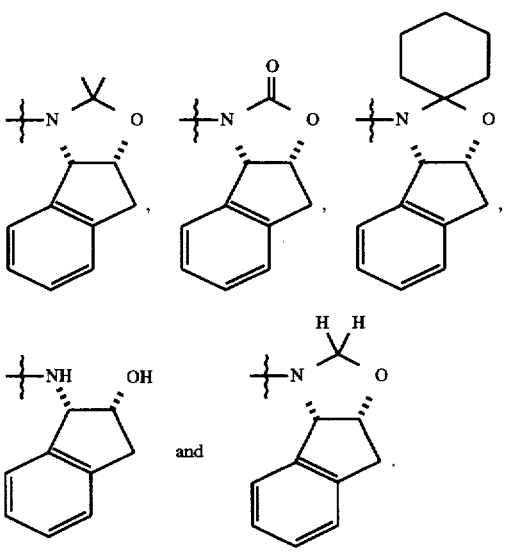

What is claimed is:

1. A method for preparing a compound of formula I

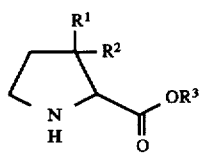

or its pharmaceutically acceptable salt, wherein:

R$^1$ and R$^2$ are independently selected from the group consisting of H, C$_{1-6}$ alkyl, and aryl, and R$^3$ is selected from the group consisting of H, C$_{1-6}$ alkyl, aryl and allyl, which comprises rearranging a compound of formula 1:

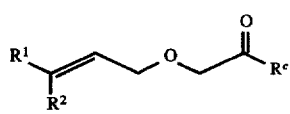

through reaction with a strong base at an initial temperature of about –100° C. to about –50° C., for about 30 minutes to about 6 hours, heating the mixture to about –50° C. to about 0° C. to provide a compound of formula Ia,

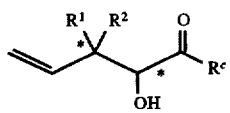

wherein:

R$^1$ and R$^2$ are described above R$^c$ is a group auxiliary and* designates a stereogenic center;

esterification of Ia with an acidic alcohol for about 30 minutes to about 3 hours to give a compound of formula 3 having a hydroxy group;

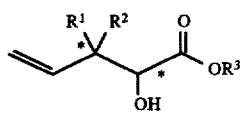

functionalization of the hydroxy group of formula 3 using a tertiary amine to provide a compound of formula 4

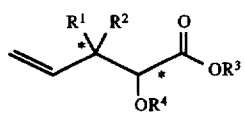

wherein

OR$^4$ is a leaving group;

displacing the OR$^4$ group of formula 4 with sodium azide in the presence of a polar aprotic solvent at a temperature of about 40° C. to about 140° C. to produce a compound of formula 5;

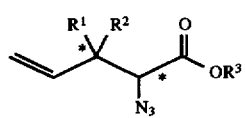

and, hydroboration and cycloalkylation of 5 with a dialkylborane reagent followed by treatment with an acid to give a compound of formula I or its pharmaceutically acceptable salt

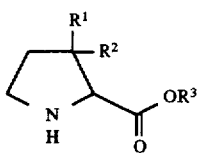

2. The method according to claim 1 wherein the strong base is selected from the group consisting of LDA, NaH, KH, LHMDS, n-BuLi, NaHMDS and KHMDS, the acidic alcohol is a 3 to 1 ratio of alcohol to acid, wherein the alcohol is selected from a group consisting of methanol, ethanol, propanol, butanol and isopropanol, the acid is selected from a group consisting of anhydrous HCl, HCl, TsOH, MsOH and sulfuric acid, the tertiary amine belongs to the group consisting of triethylamine diisopropyilethylamine, dimethylethylamine, and dimethylpentylamine, the polar aprotic solvent belongs to the group consisting of DMSO and DMF and the dialkylborane reagent belongs to a group consisting of dicyclohexylborane, and 9-BBN.

3. The method according to claim 1 which further contains an additive selected from the group consisting of Cp2ZrCl2, HMPA, TMEDA, and DMPU in the step of rearranging the compound of formula 1.

4. The method according to claim 1 wherein the chiral group is selected from the group consisting of